United States Patent [19]

Dunlop

[11] Patent Number: 5,718,240

[45] Date of Patent: Feb. 17, 1998

[54] SURGICAL AID AND METHOD OF SURGERY UTILIZING THE SURGICAL AID

[76] Inventor: Gillian Mary Dunlop, 57 Johnston Crescent, Land Cove, NSW 2066, Australia

[21] Appl. No.: 580,084

[22] Filed: Dec. 20, 1995

[30] Foreign Application Priority Data

Dec. 23, 1994 [AU] Australia .................. PN0238

[51] Int. Cl.$^6$ ............................................ A61C 5/14
[52] U.S. Cl. .................................... 128/859; 600/242
[58] Field of Search ................... 128/845, 846, 128/857, 858, 859, 860, 861; 600/226, 229, 237, 239, 242

[56] References Cited

U.S. PATENT DOCUMENTS

| | | | |
|---|---|---|---|
| 903,344 | 11/1908 | Wackler | 600/242 |
| 3,587,566 | 6/1971 | Oscarsson | 600/242 |
| 4,200,089 | 4/1980 | Inoue | 600/242 |
| 4,259,068 | 3/1981 | Stephens . | |
| 4,592,344 | 6/1986 | Scheer | 600/242 |
| 4,889,490 | 12/1989 | Jenkinson . | |
| 5,152,300 | 10/1992 | Horst . | |

FOREIGN PATENT DOCUMENTS

| | | |
|---|---|---|
| 3329919 A1 | 4/1985 | Germany . |
| 509419 | 7/1939 | United Kingdom . |
| 1 249 006 | 10/1971 | United Kingdom . |

*Primary Examiner*—Michael A. Brown
*Attorney, Agent, or Firm*—Whitham, Curtis, Whitham & McGinn

[57] ABSTRACT

The present invention relates to aids, such as a guard 1, for use in throat and oral cavity surgical operations, such as tonsillectomies, that require a surgeon to gain access via a patient's mouth, as well a method of surgery utilising such a guard 1. The guard 1 includes a first protection member 2 having a protection surface 3 and a second protection member 4 having a protection surface 5. The protection members 2 and 4 are connected by means of a spine 6. The spine portion 6 being integrally formed with the protection members 2 and 4 provides sufficient elasticity to enable the clamping ends 7 and 8 of members 2 and 3 respectively, to engage the inside and outside surfaces of a patient's mouth region to thereby reasonably attach the guard 1 to a side of a patient's mouth.

20 Claims, 4 Drawing Sheets

SURGICAL AID AND METHOD OF SURGERY UTILIZING THE SURGICAL AID

FIELD OF INVENTION

The present invention relates to aids, such as guards, for use in throat and oral cavity surgical operations, such as tonsillectomies, that require a surgeon to gain access via a patient's mouth, as well a method of surgery utilising such a guard.

BACKGROUND ART

Surgical operations on a patient's throat and oral cavity usually require access via the mouth of the patient. Mechanisms such as mouth gags and more specifically Boyle Davis mouth gags, are used to hold a patient's mouth open in order to allow a surgeon sufficient room to gain proper access to achieve the surgical objectives. Such mouth gags are generally spring biased and also include a ratchet mechanism to overcome the natural tendency of the muscles of the mouth to close.

A Boyle Davis mouth gag engages the mouth in the vicinity of the front teeth on the upper and lower jaws with the lower jaw section having a portion which projects into the patient's mouth to depress or restrain the tongue.

Such mouth gags leave parts of the lips and adjacent cheek, both inside and outside, exposed to damage if accidentally contacted by cauterising tools used during an operation. Cauterising tools such as diathermy devices can be a particular problem as the insulation around the high temperature portions of such devices deteriorates over time, and also due to sterilisation procedures. If the diathermy insulation deteriorates, the current may also pass through the defect to burn the lip and cheek with which it is in contact. Other injury may result from sharp implements or other treatments. A major difficulty with such injury is that it tends to be instantaneous.

OBJECT OF THE INVENTION

The object of the present invention is to provide a guard to protect at least a part of a patient's lip or cheek from burning or other injury which may occur from surgical or like procedures.

SUMMARY OF THE INVENTION

The present invention provides a surgical guard which includes a body portion providing at least one protection surface adapted to cooperate with at least one part of at least one of a patient's lip or cheek, the surgical guard when in use shielding said at least one part of at least one of a patient's lip or cheek from a tool being used in a surgical procedure, the guard being adapted to be releasably attached to a cheek adjacent to the lip.

It is preferred that the guard is manufactured from a sterilisable, heat resistant, flexible material such as a silicon based material or teflon.

It is preferred that the guard protects at least an outside surface of the patient's cheek.

It is preferred that the guard protects at least an inner surface of the patient's cheek.

It is preferred that the guard also includes an attachment means to releasably attach the guard to the mouth.

It is preferred that the attachment means is biased so as to provide a securing force onto the inner and outer surfaces of the patient's cheek.

Alternatively the attachment means can be adapted to be releasably attached to at least one portion of the mouth region.

Alternatively the guard can be held in position relative to a patient's mouth by engaging a patient's jaw or jaws.

It is preferred that the guard is constructed of a material which has sufficient physical properties to maintain the protective function of the guard whilst being of sufficient flexibility or plasticity to allow the guard to accommodate different shaped mouths.

Advantageously the guard can also be pre-shaped or contoured according to an ergonomic average of patient's mouth shapes and dimensions.

It is preferred that the material from which the guard is constructed will not conduct electricity.

It is preferred that the material from which the guard is constructed is heat resistant and will not burn or melt if it comes into contact with hot objects.

It is preferred that if a material is used that will melt or burn, a protective layer which is heat resistant is located so as to rest against a patient's lip or cheek.

It is preferred that the guard is constructed from a sterilisable material in order to properly sterilise the guard before use.

It is preferred that the material from which the guard is constructed is crack resistant.

It is preferred that the guard is constructed to prevent any surfaces mating or providing pockets which may form traps thereby limiting the sterilisation effectiveness.

It is preferred that all the protection surfaces and features of the guard are constructed integrally with each other.

It is preferred that the guard is provided with handle means to allow for easy application and removal of the guard by surgical staff.

It is preferred that the guard is manufactured in reusable or single use form.

The invention further provides a method of performing a surgical procedure on a patient via a patients mouth, said method including a step in the preparation of the patient or during the surgical procedure which includes the attachment of a surgical guard, described in the paragraphs above.

The features of the invention provide a guard which is readily useable during operations [and when manufactured from a sterilisable material is reusable], to provide protection for the exposed surfaces of either the cheeks, lips and mouth or a combination of these, whilst at the same time ensuring a surgeon using the guard has unobstructed access to the patient's throat and oral cavity. When a guard of the present invention is used it changes the instantaneous character of a potential injury into one which can be dealt with before actual injury occurs.

BRIEF DESCRIPTION OF THE DRAWINGS

An embodiment of the present invention will now be described by way of example only with reference to the accompanying drawings in which.

DETAILED DESCRIPTION OF DRAWINGS

Figure 1:
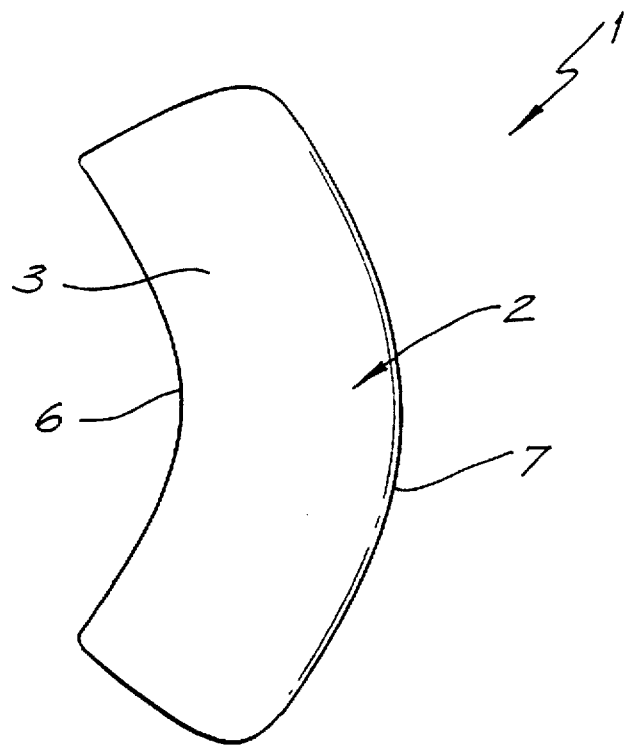
FIG. 1 is a plan view of an embodiment of the present invention.
Figure 2:
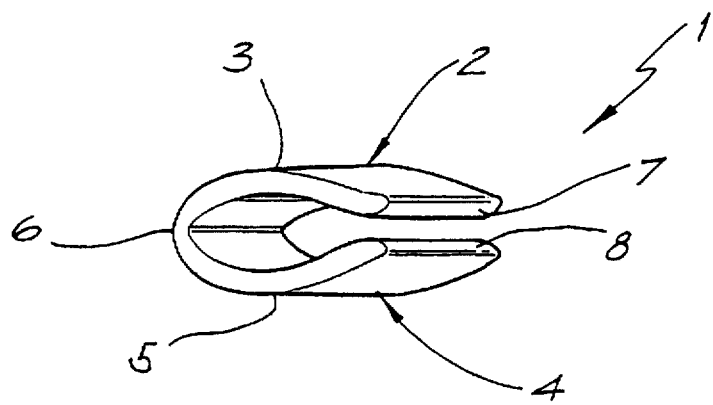
FIG. 2 is side elevation of the apparatus of FIG. 1.

In FIGS. 1 and 2, a guard 1 includes a first protection member 2 having a protection surface 3 and a second protection member 4 having a protection surface 5. The protection members 2 and 4 are connected by means of a spine 6. The spine portion 6 is integrally formed with the protection members 2 and 4. The spine portion 6 provides sufficient elasticity to enable the clamping ends 7 and 8 of members 2 and 3 respectively, to engage the inside and outside surfaces of a patient's mouth region to thereby releasably attach the guard 1 to a side of a patient's mouth. When the guard 1 is positioned on a patient, the spine 6 will effectively protect the patient's lips, whilst protection members 2 and 4 will protect the inside and outside portions of the patient's cheeks which are located adjacent the patient's lips.

The clamping ends 7 and 8 do not quite engage each other when the guard 1 is not in use. By ends 7 and 8 not engaging each other, both ends 7 & 8 are ready sterilisable. It can also be observed that the guard 1 does not include any other mating surfaces or pocket or trap forming regions. This renders the guard 1 reusable once it is fully sterilised by autoclave means. However, it is envisaged that the guard 1 can be manufactured such that it is a disposable item of hospital or surgical inventory.

The guard 1 can be manufactured from any appropriate material, such as silicon based materials; a temperature-resistant, teflon-based material; or other materials which are approved for use in autoclaves and surgical operations. If the guard 1 is to be used in conjunction with cauterising implements, then the material selected must be heat resistant and not able to be burned. If the guard 1 is to be used in conjunction with cutting implements other materials such as stainless steel, polymeric materials, or any other suitable material can be used.

If a material that melts is to be used, either of two constructions can be adopted. In a first construction, if the material can melt, a sufficient thickness of material is provided so that as soon as a surgeon has detected the contact, if contact is made, then breaking contact can be made before sufficient heat has been transferred to the patient's lip. In a second construction, the guard 1 is constructed from two layers of material, a first layer of a meltable material and a second layer of heat resistant or non melting material. The heat resistant or non melting material need not be very thick, but sufficient to protect the patient's cheek or lip.

By constructing the guard 1 out of silicon based materials, the guard 1 will have sufficient plasticity to be shaped, when in use, to the contours of a patient's mouth. If a sufficiently soft material is utilised, the guard 1 can be cut to length immediately prior to surgery. In this way a "one guard fits all" is produced.

Figure 3:
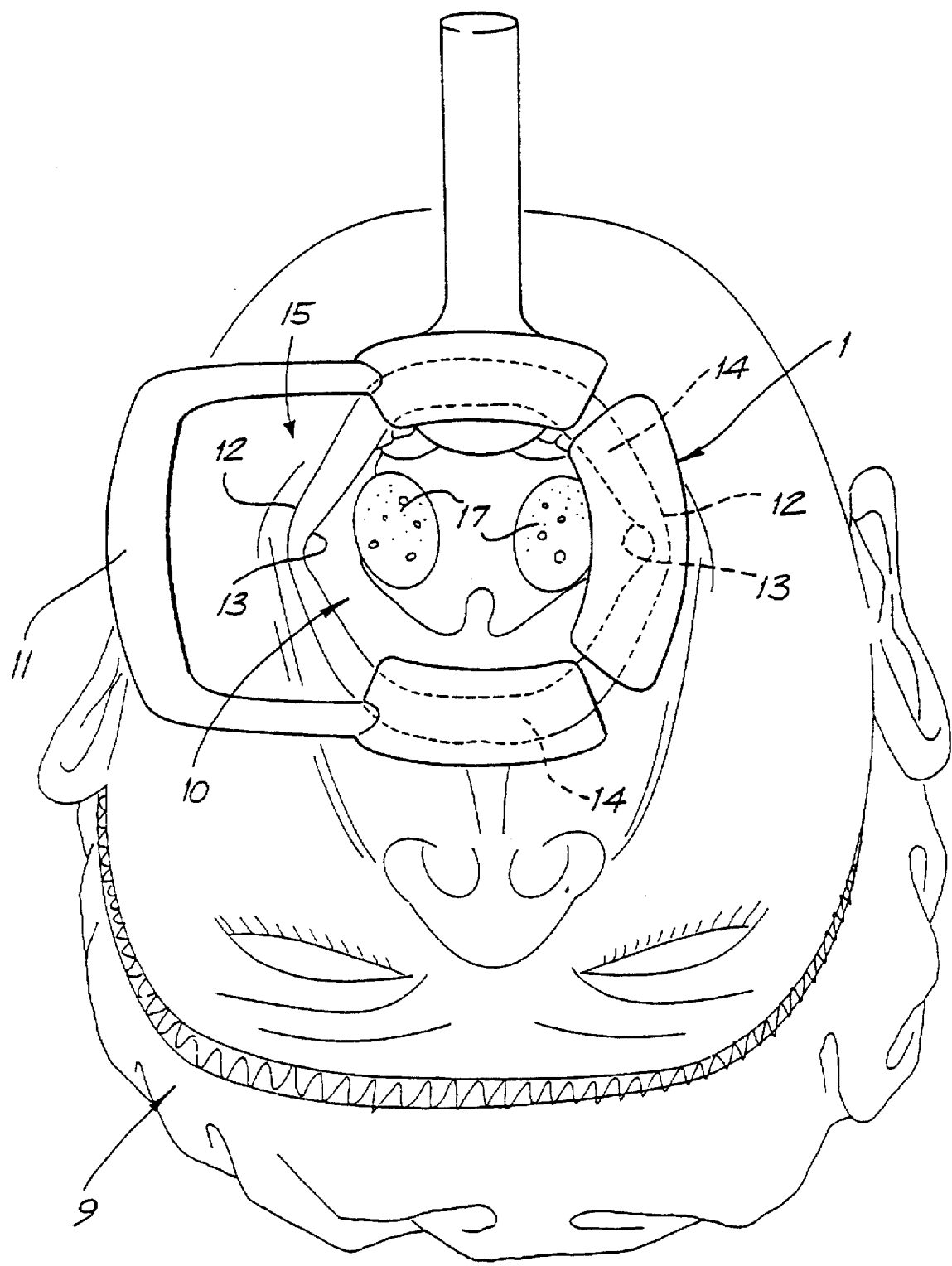
FIG. 3 is a plan view of a patient's mouth utilising the apparatus if FIG. 1.

Alternatively, if a stiffer plastics material or a metal such as stainless steel is utilised in the manufacture of the guard 1, the guard 1 can be moulded with a curved portion in three orthogonal planes as is illustrated in FIGS. 1, 2 and 3. It can be seen that the spine 6 is curved whilst both protection member 2 & 4 are also curved. The guard of FIG. 1 is also curved into the page, and this is more clearly illustrated in FIG. 3. In this case a variety of sizes of guards 1 can be produced and then selected for use according to the age of the patient and the approximate size of the patient's mouth. In this situation a good match of the patient's mouth size to the length of the guard 1 may not be present, but a sufficient area of lip and or inside and or outside surface of a patient's cheek can be protected for the guard 1 to function effectively.

No matter what material is used the amount of spring tension available at the clamping ends 7 & 8 has to be sufficient to hold the guard in place, whilst not injuring the patient's mouth region.

In FIG. 3 is illustrated a plan view of a part of a patient's head 9, having a mouth 10. A Boyle Davis mouth gag 11 is positioned in the mouth 10 to thereby hold the mouth 10 in a fully opened condition. In this way, tonsils 17 are fully accessible to the surgeon. To protect the exposed regions 12 and 13 of the lips 14 and cheeks 15 of the open mouth 10, the guard 1 is positioned over a lip 14 and cheek 15. The lip 14 of the patient is passed between the clamping ends 7 & 8 until the a part of the lip 14 makes contact with an internal portion corresponding to the spine 6. The clamping ends 7 & 8 then compress the cheek 15 of the patient to hold the guard 1 in place.

Another guard 1 (not illustrated) can be placed over the other lip 14 and cheek 15 to ensure that both sides are protected.

It is readily observed from FIGS. 1, 2 and 3 that the guard 1 is relatively streamline in shape. This helps to prevent the guard 1 from occluding or reducing the mouth opening when the guard 1 is in place.

If desired, the guard 1 can be manufactured from a length of suitable tubing, in which case the spine 6 is located opposite the clamping ends 7 and 8.

Figure 4:
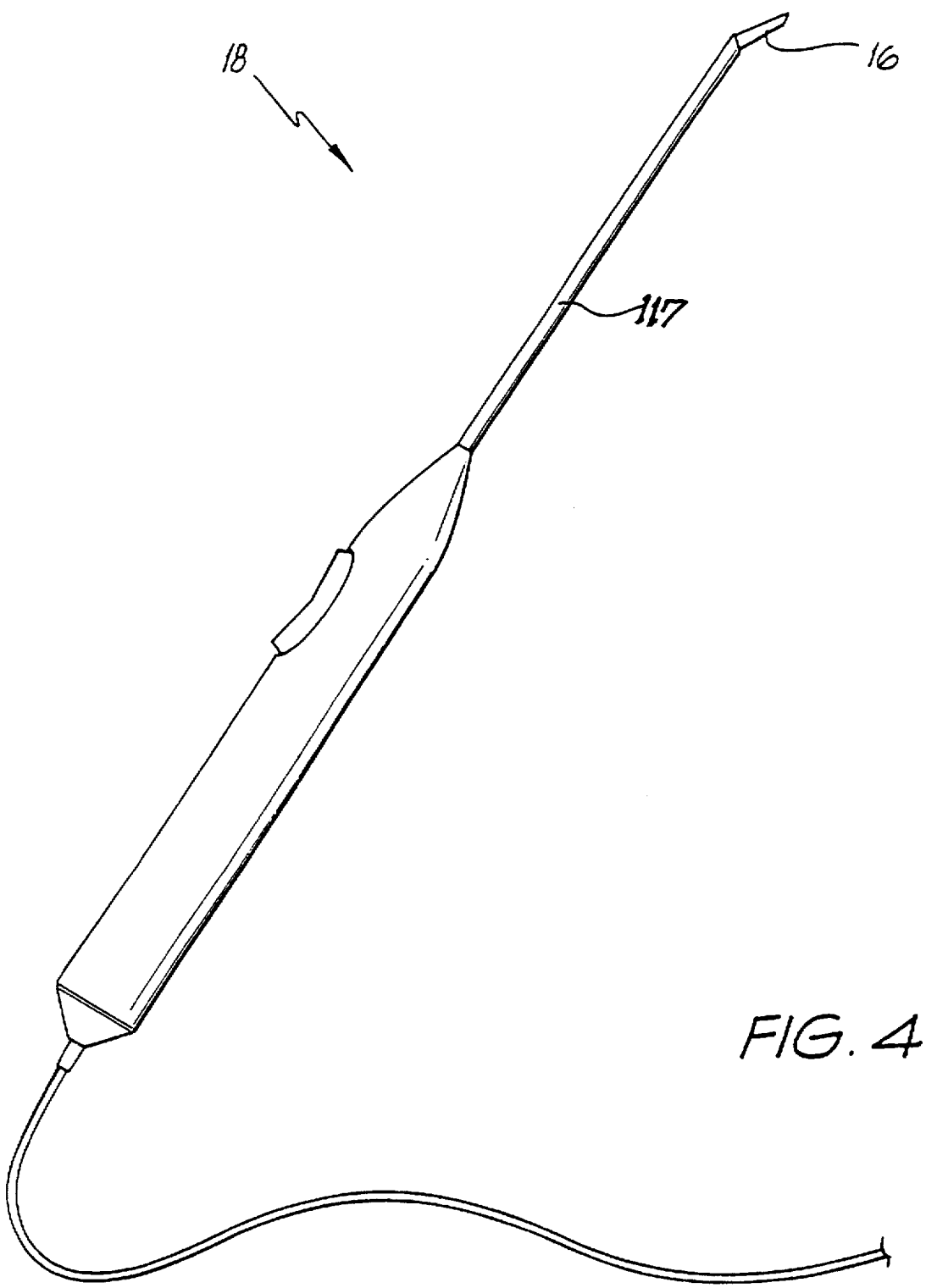
FIG. 4 is a side view of a Diathermy device.

In FIG. 4 there is illustrated a diathermy device 18 which has a thermally insulated portion 117 and an exposed tip 16 which is allowed to heat up to a sufficient temperature to cauterise any incisions made when the tonsils are surgically removed. It will be noticed that the thermally insulated portion 117 is of a considerable length, as the device has to be able to reach a considerable distance down a patient's mouth 10 and throat. With the guard 1 in position on the wall 14, if the thermally insulated portion 117 should be damaged, exposing a high temperature surface, this surface will not cause any burning or damage to the lips or parts of the adjacent internal surface of the mouth, as the diathermy device is pivoted, rotated, manipulated and orientated by the surgeon so as to most effectively position the tip 16 to properly cauterise the area. Sometimes, the thermally insulated portion 117 is used to depress the lip of the mouth to better position the cauterising tip 16, and in this situation the surgeon can be confident of causing no injury to the patient's lip from the diathermy device 18, when the guard 1 is in position and is sandwiched between the insulated portion 117 and the patient's lip.

Figure 5:
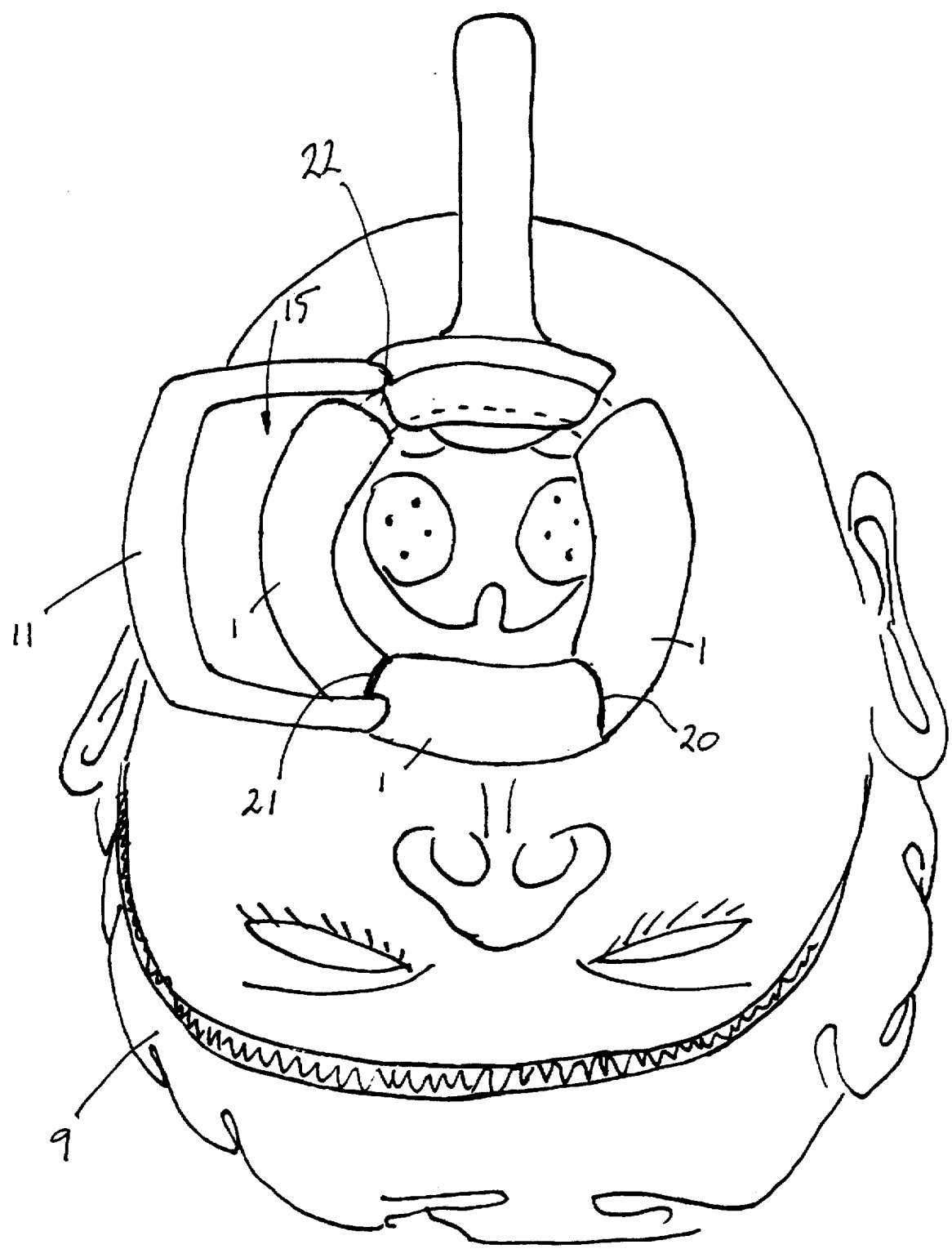
FIG. 5 is a modified version of the guard illustrated in FIG. 3.

A modified version of the guard 1, (as illustrated in FIG. 5), can be manufactured from a single piece having four protective sides and being open top and bottom, there being three joins 20,21,22 so that a quasi-rectangular guard is formed which has a break between a first and fourth side. The four sides thus respectively engage, internally, the upper and lower jaws, or the internal walls of the sides of the mouth. The construction of such a guard such that some bias is provided by the shape and material which will allow the four sided guard to exert a force against any two opposing mouth formations, such as upper and lower jaws, or the two internal sides of the mouth, to thereby hold the guard in position.

A further improvement of the guard 1 is to provide it with handles (not illustrated) so that surgical staff can readily apply or remove the guard. It is envisaged that whilst the guards described above are manufactured so that the portions of the guard are integrally formed, a fabricated guard can be made, however special care needs to be taken to ensure that no non-sterilisable portions exist in the guard.

The construction and form of the guard, if it is meant to be sterilisable, should be constructed to prevent any surfaces mating or providing pockets which may form traps thereby limiting sterilisation effectiveness. Also for sterilisation purposes, the material chosen for the construction of the guard should be crack-resistant.

Modifications can be made to embodiments of the present invention by persons skilled in the art with out departing from the scope of the present invention.

I claim:

1. A surgical guard including
a mechanism for engaging the mouth of a patient in the vicinity of front teeth of the patient and including means for holding open the mouth of the patient, and
means for providing at least one protective surface for a part of a patient's lip or cheek exposed by said mechanism and adapted to be releasably attached to a cheek adjacent to the lip said means for providing at least one protective surface including two curved resilient arms extending from a spine, ends of each said arm opposite said spine including inwardly extending gripping ends.

2. A guard as claimed in claim 1 which is manufactured from a sterilisable, heat resistant, flexible material.

3. A guard as claimed in claim 1 which is manufactured from a silicon based material or teflon.

4. A guard as claimed in claim 1 wherein said guard is manufactured from a meltable material and a sufficient thickness is provided to give a surgeon time to remove a source of heat without injury.

5. A guard as claimed in claim 1 wherein said guard is manufactured in part from a meltable material and a layer of heat resistant or other protective material is positioned so as to be in contact with the patient's lips or cheek.

6. A guard as claimed in claim 1 wherein the guard protects at least an outside surface of a patient's cheek.

7. A guard as claimed in claim 1, wherein the guard protects at least an inner surface of a patient's cheek.

8. A guard as claimed in claim 1 wherein the guard also includes an attachment means to releasably attach the guard to the mouth.

9. A guard as claimed in claim 8, wherein the attachment means is adapted to be releasably attached to at least one portion of the mouth region.

10. A guard as claimed in claim 8, wherein the guard is held in position relative to a patient's mouth by engaging a patient's jaw or jaws.

11. A guard as claimed in claim 1, wherein the material from which the guard is constructed will not conduct electricity.

12. A guard as claimed in claim 1, wherein the guard is constructed from a sterilisable material in order to properly sterilise the guard before use.

13. A guard as claimed in claim 1, wherein the material from which the guard is constructed is crack resistant.

14. A guard as claimed in claim 1, wherein the guard is constructed to prevent any surfaces mating or providing pockets which may form traps thereby limiting the sterilisation effectiveness.

15. A guard as claimed in claim 1, wherein all the protection surfaces and features of the guard are constructed integrally with each other.

16. A guard as claimed in claim 1, wherein the guard is provided with handle means to allow for easy application and removal of the guard by surgical staff.

17. A guard as recited in claim 1, wherein said means for providing a protective surface is joined to said mechanism.

18. A guard as recited in claim 1, wherein an end of said means for providing a protective surface is shaped to cooperate with an end of a portion of said mechanism which engages the mouth of the patient.

19. A method of performing oral surgery including the steps of
engaging the mouth of a patient in the vicinity of front teeth of the patient with a mechanism for holding open the mouth of the patient, and
covering a portion of the lip or cheek of the patient which is exposed by said mechanism with a protective surface which engages said portion of the lip or cheek of the patient with gripping ends of two curved arms disposed on opposing side of a spine.

20. A method as recited in claim 19 wherein said spine is a curved spine.

* * * * *

UNITED STATES PATENT AND TRADEMARK OFFICE
CERTIFICATE OF CORRECTION

PATENT NO.   : 5,718,240
DATED        : February 17, 1998
INVENTOR(S)  : Dunlop

It is certified that error appears in the above-identified patent and that said Letters Patent is hereby corrected as shown below:

Columns 5 and 6 should be deleted to appear as per attached columns 5 and 6

Signed and Sealed this

Twenty-fourth Day of November, 1998

Attest:

BRUCE LEHMAN

Attesting Officer

Commissioner of Patents and Trademarks

The construction and form of the guard, if it is meant to be sterilisable, should be constructed to prevent any surfaces mating or providing pockets which may form traps thereby limiting sterilisation effectiveness. Also for sterilisation purposes, the material chosen for the construction of the guard should be crack-resistant.

Modifications can be made to embodiments of the present invention by persons skilled in the art with out departing from the scope of the present invention.

I claim:

1. A surgical guard including
means for providing at least one protective surface for a part of a patient's lip or cheek and adapted to be releasably attached to a cheek adjacent to the lip said means for providing at least one protective surface including two curved resilient arms extending from a spine, ends of each said arm opposite said spine including inwardly extending gripping ends.

2. A guard as claimed in claim 1 which is manufactured from a sterilisable, heat resistant, flexible material.

3. A guard as claimed in claim 1 which is manufactured from a silicon based material or teflon.

4. A guard as claimed in claim 1 wherein said guard is manufactured from a meltable material and a sufficient thickness is provided to give a surgeon time to remove a source of heat without injury.

5. A guard as claimed in claim 1 wherein said guard is manufactured in part from a meltable material and a layer of heat resistant or other protective material is positioned so as to be in contact with the patient's lips or cheek.

6. A guard as claimed in claim 1 wherein the guard protects at least an outside surface of a patient's cheek.

7. A guard as claimed in claim 1, wherein the guard protects at least an inner surface of a patient's cheek.

8. A guard as claimed in claim 1 wherein the guard also includes an attachment means to releasably attach the guard to the mouth.

9. A guard as claimed in claim 8, wherein the attachment means is adapted to be releasably attached to at least one portion of the mouth region.

10. A guard as claimed in claim 8, wherein the guard is held in position relative to a patient's mouth by engaging a patient's jaw or jaws.

11. A guard as claimed in claim 1, wherein the material from which the guard is constructed will not conduct electricity.

12. A guard as claimed in claim 1, wherein the guard is constructed from a sterilisable material in order to properly sterilise the guard before use.

13. A guard as claimed in claim 1, wherein the material from which the guard is constructed is crack resistant.

14. A guard as claimed in claim 1, wherein the guard is constructed to prevent any surfaces mating or providing pockets which may form traps thereby limiting the sterilisation effectiveness.

15. A guard as claimed in claim 1, wherein all the protection surfaces and features of the guard are constructed integrally with each other.

16. A guard as claimed in claim 1, wherein the guard is provided with handle means to allow for easy application and removal of the guard by surgical staff.

17. A guard as recited in claim 1, wherein said means for providing a protective surface is joined to said mechanism.

18. A guard as recited in claim 1, wherein an end of said means for providing a protective surface is shaped to cooperate with an end of a portion of said mechanism which engages the mouth of the patient.

19. A guard as claimed in claim 1, further indulging a mechanism for engaging the mouth of a patient in the vicinity of front teeth of the patient and including means for holding open the mouth of the patient, and wherein said means for providing at least one protective surface covers a part of the patient's lip or cheek exposed by said mechanism.

20. A method of performing oral surgery including the steps of engaging the mouth f a patient in the vicinity of front teeth of the patient with a mechanism for holding open the mouth of the patient, and
covering a portion of the lip or cheek of the patient which is exposed by said mechanism with a protective surface which engages said portion of the lip or cheek of the patient with gripping ends of two curved arms disposed on opposing side of a spine.

21. A method as recited in claim 19 wherein said spine is a curved spine.

* * * * *